United States Patent [19]

Callaghan et al.

[11] Patent Number: 4,577,491

[45] Date of Patent: Mar. 25, 1986

[54] METHOD FOR DETERMINING THE STABILITY OF FOAM

[75] Inventors: Ian C. Callaghan, Wokingham; Clive M. Gould, Staines, both of England

[73] Assignee: The British Petroleum Company, p.l.c., London, England

[21] Appl. No.: 666,651

[22] Filed: Oct. 31, 1984

[30] Foreign Application Priority Data

Nov. 5, 1983 [GB] United Kingdom ................. 8329624

[51] Int. Cl.⁴ .......................................... G01N 33/22
[52] U.S. Cl. .................................................. 73/60.1
[58] Field of Search .......................... 73/60.1, 64.2, 19

[56] References Cited

U.S. PATENT DOCUMENTS 4,301,676 11/1981 Gokcen ............................ 73/64.2

FOREIGN PATENT DOCUMENTS 505916 10/1976 U.S.S.R. ............................. 73/64.2
605152  4/1978 U.S.S.R. ............................. 73/64.2
619626  8/1978 U.S.S.R. ............................... 73/19
705303 12/1979 U.S.S.R. ............................... 73/19

Primary Examiner—Stewart J. Levy
Assistant Examiner—Joseph W. Roskos
Attorney, Agent, or Firm—Morgan, Finnegan, Pine, Foley & Lee

[57] ABSTRACT

A method for determining the stability of live foam comprises a sample pressurizing vessel connected to a sample injection chamber leading to a sample cell linked to a reference cell maintained at constant pressure. The link between the sample cell and the reference cell comprises a link fitted with a valve for initially equalizing the pressure between the two and subsequently isolating them. A differential pressure transducer is provided for determining the subsequent change in pressure of the sample with reference to the reference cell as the foam collapses.

1 Claim, 1 Drawing Figure

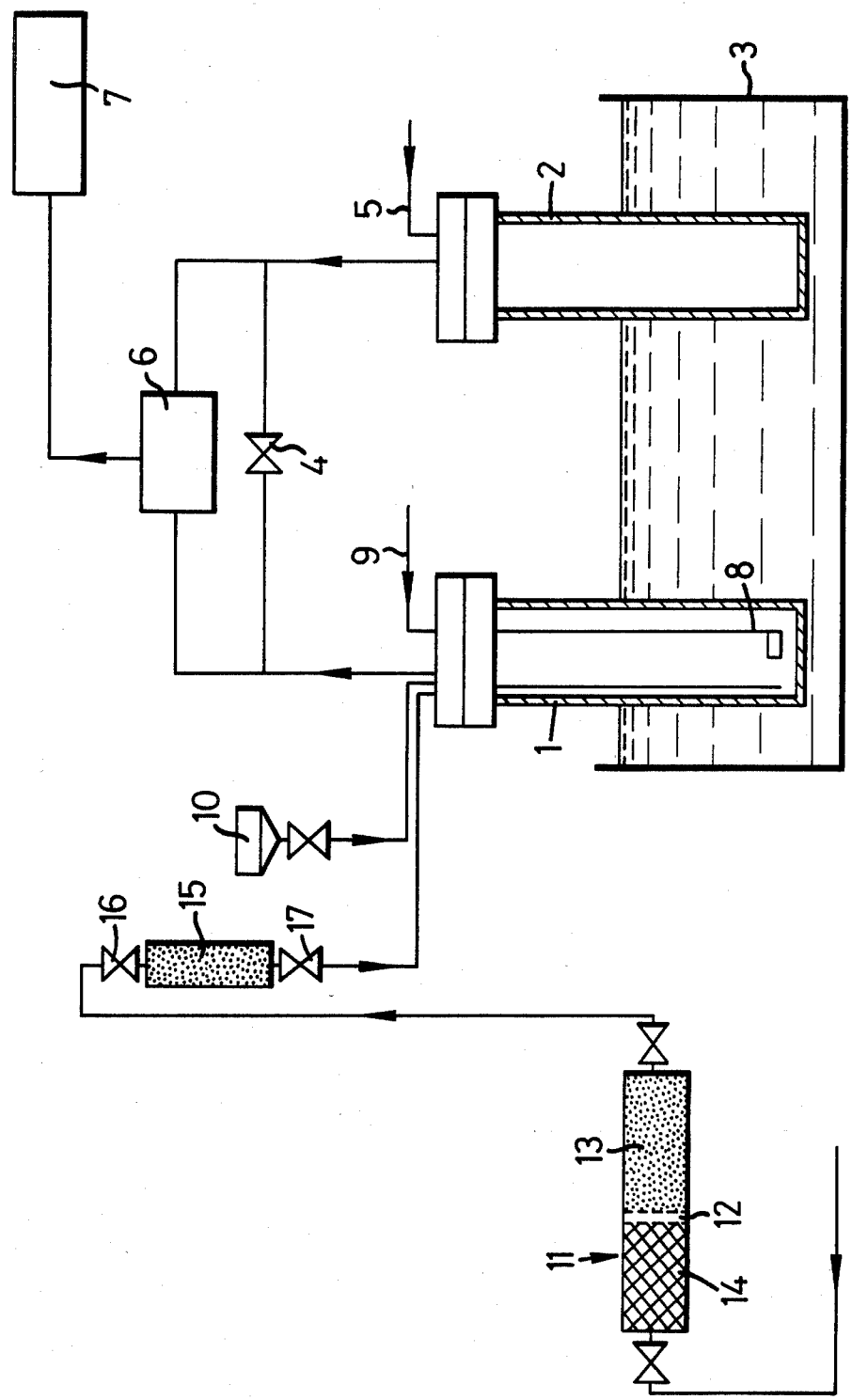

METHOD FOR DETERMINING THE STABILITY OF FOAM

This invention relates to a cell for determining the stability of a foam, particularly a foam resulting from the release of pressure on live crude oil.

Foams occur in many situations and may be beneficial, such as those used in fire fighting and froth flotation, or harmful such as those occurring in gas oil separators and distillation columns.

When oil is produced from a well, it is forced by pressure from the reservoir up the well to the surface. As the oil rises, the pressure becomes less and gas associated with the oil is progressively released from solution.

After emerging from the well, it is usually necessary to treat the mixture of liquid oil and gas to remove free gas and dissolved gas which may come out of solution when the oil is maintained near atmospheric pressure, for example, during transport in a tanker.

Separation may be carried out near the wellhead or at a distant location after the oil and gas have been pumped under high pressure through a pipeline.

Separation is effected in a vessel known as a separator. Various types of separators are known. One common type is the horizontal separator which comprises a horizontal cylinder containing a system of baffles, defoamers and mist extractors. The crude enters at one end and flows towards an outlet at the other end. During the time it takes to do this, the gas bubbles out of solution and leaves the separator by a gas outlet at the top.

Sometimes the crude oil and gas form a stable foam in separators, particularly under high throughput conditions, with the result that liquid oil carries over in the gas stream.

Stable foams are of two types, known as stabilised and live foams respectively. A stabilised foam is one created by the passage of gas through a liquid. A live foam is created by gas dissolved within a liquid escaping when the liquid is subjected to a sudden pressure drop.

The stability of a foam depends on two main factors: the tendency of the liquid to drain from the foam and the resistance of the foam bubbles to rupture.

In certain instance it is advantageous to inject an anti-foam additive, eg, a silicone, into the oil stream before it enters the separator. This additive destabilises the foam and in effect increases the handling capacity of the separator.

Additives, of course, vary in their activity, depending to some extent on their intrinsic properties and to some extent on the environment in which they operate, particularly the composition of the crude oil.

Ross and Nishioka, Journal of Colloid and Interface Science, Vol 81, Page 1, 1981 disclose unpressurised equipment for determining the stability of stabilised aqueous foams.

We have now devised equipment which is suitable for use in determining the stability of live and optionally stabilised foam and hence the efficiency of anti-foam agents.

According to the present invention there is provided apparatus for determining the stability of live foam which apparatus comprises a sample pressurising vessel connected to a sample injection chamber leading to a sample cell linked to a reference cell maintained at constant pressure, the link between the sample cell and the reference cell comprising a line fitted with a valve for initially equalising the pressure between the two and subsequently isolating them, and a differential pressure transducer for determining the subsequent change in pressure of the sample cell with reference to the reference cell.

When a foam within a vessel collapses, the gas under pressure entrapped by the liquid is released and hence the pressure within the vessel rises.

The sample pressurising vessel may be pressurised by means of a hydropump.

The sample cell and the reference cell are preferably maintained in a thermostatically controlled bath.

For stabilised foam samples, an additional sample introduction system is provided which may simply be a valve-controlled line for the entry of liquid. In this case the sample cell must also contain means for the distribution of gas through it.

The apparatus is particularly suitable for determining the stability of non aqueous live foams such as crude oil/gas foams.

Thus according to another aspect of the present invention there is provided a method for determining the stability of a live crude oil/gas foam which method comprises the steps of:

(a) pressurising a sample of crude oil containing gas,
(b) introducing the sample into a sample cell connected to a reference cell initially at the same pressure,
(c) reducing the pressure on the sample whereby a foam is generated,
(d) isolating the sample cell and the reference cell when the foam has developed, and
(e) determining the subsequent change in pressure of the sample cell with reference to the reference cell.

The invention is illustrated with reference to the accompanying drawing which is a schematic flow diagram showing the use of the apparatus for determining the stability of foam.

The core of the apparatus contains a sample cell 1 and a reference cell 2, situated in a thermostatically controlled water bath 3. A change in pressure in the sample cell can be compared with the constant pressure of the reference cell. The two cells can be isolated from each other by closing valve 4. Valve 4 may be operated by a solenoid when the foam is fully developed in sample cell 1. A nitrogen booster 5 is connected to the reference cell 2 to enable the cells 1 and 2 to be pressurised. The cells are connected to a differential pressure transducer 6 wired to a chart recorder 7.

The sample cell incorporates a tun dish 10 which is a sample introduction point for stabilised foam experiments. A sinter 8 is situated within the sample cell 1 which is connected to the ring main nitrogen 9.

A high pressure vessel 11 is connected to the sample cell 1 and enables live crude samples at pipeline pressures to be introduced to the cell.

The vessel 11 contains a piston 12, on one side of which is located the crude oil sample 13 which is pressurised by pumping water 14 into the opposite side of the piston. The sample injection vessel 15 has a volume of 100 ml to ensure that a constant volume of sample is always injected into the sample cell at a time. The vessel is isolated by closing valves 16 and 17.

An endoscope (now shown) may be provided in the cell 1 to provide a visual indication of the foam and its subsequent collapse.

In an attempt to simulate conditions met by crude oil during first stage separation, foams are generated by subjecting the crude oil to a pressure drop equivalent to that met by the oil on entry to a gas oil separator. The crude oil is bought to a pressure simulating pipeline conditions using a hydropump.

In order to restore the crude oil to the phase condition in the pipeline the vessel 11 is agitated using a rocking lever and then repressurised since the pressure drops as the gas dissolves in the oil phase. The sample and reference cells are left at atmospheric pressure in order to give an equivalent pressure drop to that of separation. The oil is then injected into the sample injection vessel 15 with valve 17 closed at this stage. The system requires repressurising due to the volume increase and valve 16 is then closed. The sample is then injected into the sample cell 1 by opening valve 17. When all the oil from the injection vessel enters the sample cell 1, valve 17 is closed followed by valve 4. Pressure changes are detected by the pressure transducer 6 and observed on the chart recorder 7.

Alternatively, the sample cell 1 and the reference cell 2 may be fitted with pressure relief valves and the sample may be injected into the cell still under high pressure with the pressure subsequently being released.

This method of operation avoids foaming of the sample in the line between the injection vessel 15 and the cell 1.

This invention is illustrated further with reference to the following examples.

EXAMPLE 1

A sample of a North Sea crude oil (SG=0.827 was taken at a line pressure of 120 bar. It was then re-equilibrated in the high pressure foam rig hereinbefore described. A 100 ml aliquot was transferred via the injection vessel 15 to the sample cell 1 at 120 bar. The vessel and cell were then isolated from each other, the pressure in the cell was reduced to 3.5 bar and a foam was allowed to develop fully.

When foam generation had ceased, as observed through an endoscope, the sample cell 1 and reference cell 2 were isolated from each other and the rate of increase of pressure in the former relative to the latter was recorded.

From the $\Delta P$-time trace, the half life of the foam was estimated to be 12 seconds.

EXAMPLE 2

A sample of a North Sea crude oil (5.6=0.842) was reduced in pressure from 29 bar to atmospheric pressure. A foam was created in the sample cell which existed for 7 minutes before total collapse. The total collapse was determined by recording the $\Delta P$-time trace as before.

EXAMPLE 3

Example 2 was repeated with the difference that a drop of a fluorocarbon anti-foam agent was added to the sample cell to give a concentration of 2.5 ppm. The foam collapsed within 12 seconds.

We claim:

1. A method for determining the stability of a live crude oil/gas foam which method comprises the steps of
    (a) pressurising a sample of crude oil containing gas,
    (b) introducing the sample into a sample cell connected to a reference cell initially at the same pressure,
    (c) reducing the pressure on the sample whereby a foam is generated,
    (d) isolating the sample cell and the reference cell when the foam has developed and
    (e) determining the subsequent change in pressure of the sample cell with reference to the reference cell.

* * * * *